(12) United States Patent
Dunbar et al.

(10) Patent No.: US 8,579,953 B1
(45) Date of Patent: Nov. 12, 2013

(54) DEVICES AND METHODS FOR THERAPEUTIC HEAT TREATMENT

(76) Inventors: Peter J. Dunbar, Mercer Island, WA (US); Charles Chabal, Bellevue, WA (US)

( * ) Notice: Subject to any disclaimer, the term of this patent is extended or adjusted under 35 U.S.C. 154(b) by 480 days.

(21) Appl. No.: 12/330,495

(22) Filed: Dec. 8, 2008

Related U.S. Application Data

(60) Provisional application No. 61/012,400, filed on Dec. 7, 2007.

(51) Int. Cl.
*A61F 7/00* (2006.01)
*A61F 7/12* (2006.01)

(52) U.S. Cl.
USPC .............................................. 607/96; 607/99

(58) Field of Classification Search
USPC ........ 607/96, 99, 108, 98, 112; 219/528, 480; 602/2, 48
See application file for complete search history.

(56) References Cited

U.S. PATENT DOCUMENTS

| | | | |
|---|---|---|---|
| 1,377,158 A | 5/1921 | Radisson | |
| 3,857,397 A | 12/1974 | Brosseau | |
| 4,107,509 A | 8/1978 | Scher et al. | |
| 4,201,218 A | 5/1980 | Feldman et al. | |
| 4,245,149 A | 1/1981 | Fairlie | |
| 4,279,255 A | 7/1981 | Hoffman | |
| 4,303,074 A | 12/1981 | Bender | |
| 4,310,745 A | 1/1982 | Bender | |
| 4,348,584 A | 9/1982 | Gale et al. | |
| 4,396,011 A | 8/1983 | Mack et al. | |
| 4,398,535 A | 8/1983 | Guibert | |
| 4,518,851 A | 5/1985 | Oppitz | |
| 4,575,097 A * | 3/1986 | Brannigan et al. | 607/112 |
| 4,736,088 A | 4/1988 | Bart | |
| 4,930,317 A | 6/1990 | Klein | |
| 5,097,828 A | 3/1992 | Deutsch | |
| 5,138,138 A * | 8/1992 | Theilacker et al. | 219/528 |
| 5,336,255 A | 8/1994 | Kanare et al. | |
| 5,447,530 A | 9/1995 | Guibert et al. | |
| 5,451,747 A | 9/1995 | Sullivan et al. | |
| 5,580,350 A | 12/1996 | Guibert et al. | |

(Continued)

FOREIGN PATENT DOCUMENTS

| | | |
|---|---|---|
| KR | 100915320 | 9/2009 |
| WO | WO-8702891 A1 | 5/1987 |
| WO | WO-2005/079295 | 9/2005 |
| WO | WO-2006086513 | 8/2006 |

OTHER PUBLICATIONS

International Search Report and Written Opinion, International Application No. PCT/US06/04506, Applicant: Carewave, Inc., mailed Sep. 25, 2007, 7 pages.

(Continued)

*Primary Examiner* — Theodore J Stigell
*Assistant Examiner* — Brooke Matney
(74) *Attorney, Agent, or Firm* — Perkins Coie LLP

(57) ABSTRACT

Devices and methods for providing therapeutic heating are disclosed herein. In one embodiment, the system includes a device body configured to provide heat to a portion of skin. The device body also includes a low-level heating region and a high-level heating area. The low-level heating region provides a continuous amount of heat at a first temperature, and the high-level heating area provides an intermittent amount of heat at a second temperature greater than the first temperature.

14 Claims, 8 Drawing Sheets

(56) References Cited

U.S. PATENT DOCUMENTS

| | | |
|---|---|---|
| 5,601,618 A | 2/1997 | James |
| 5,658,583 A | 8/1997 | Zhang et al. |
| 5,735,889 A | 4/1998 | Burkett et al. |
| 5,741,318 A | 4/1998 | Ouellette et al. |
| 5,817,145 A | 10/1998 | Augustine et al. |
| 5,837,005 A | 11/1998 | Viltro et al. |
| 5,860,945 A | 1/1999 | Cramer et al. |
| 5,891,189 A | 4/1999 | Payne, Jr. |
| 5,893,991 A | 4/1999 | Newell |
| 5,906,637 A | 5/1999 | Davis et al. |
| 5,925,072 A | 7/1999 | Cramer et al. |
| 5,947,914 A | 9/1999 | Augustine |
| 5,964,721 A | 10/1999 | Augustine |
| 5,964,723 A | 10/1999 | Augustine |
| 5,984,995 A | 11/1999 | White |
| 5,986,163 A | 11/1999 | Augustine |
| 6,010,527 A | 1/2000 | Augustine et al. |
| 6,013,097 A | 1/2000 | Augustine et al. |
| 6,045,518 A | 4/2000 | Augustine |
| 6,066,164 A | 5/2000 | Macher et al. |
| 6,096,067 A | 8/2000 | Cramer et al. |
| 6,110,197 A | 8/2000 | Augustine et al. |
| 6,113,561 A | 9/2000 | Augustine |
| 6,146,732 A | 11/2000 | Davis et al. |
| 6,213,966 B1 | 4/2001 | Augustine |
| 6,217,535 B1 | 4/2001 | Augustine |
| 6,235,049 B1 | 5/2001 | Nazerian |
| 6,241,697 B1 | 6/2001 | Augustine |
| 6,248,084 B1 | 6/2001 | Augustine et al. |
| 6,264,622 B1 | 7/2001 | Augustine |
| 6,267,740 B1 | 7/2001 | Augustine et al. |
| 6,290,661 B1 * | 9/2001 | Cutler et al. .................... 601/49 |
| 6,293,917 B1 | 9/2001 | Augustine et al. |
| 6,328,909 B1 | 12/2001 | Kross et al. |
| 6,353,211 B1 | 3/2002 | Chen |
| 6,406,448 B1 | 6/2002 | Augustine |
| 6,407,307 B1 | 6/2002 | Augustine |
| 6,419,651 B1 | 7/2002 | Augustine |
| 6,423,018 B1 | 7/2002 | Augustine |
| 6,465,709 B1 | 10/2002 | Sun et al. |
| 6,468,295 B2 | 10/2002 | Augustine et al. |
| 6,572,871 B1 | 6/2003 | Church et al. |
| 6,580,012 B1 | 6/2003 | Augustine et al. |
| 6,605,012 B2 | 8/2003 | Muller |
| 6,710,313 B1 | 3/2004 | Asami et al. |
| 6,840,915 B2 | 1/2005 | Augustine |
| 6,893,453 B2 | 5/2005 | Agarwal et al. |
| 6,921,374 B2 | 7/2005 | Augustine |
| 6,964,787 B2 | 11/2005 | Swart et al. |
| 7,871,427 B2 * | 1/2011 | Dunbar et al. .................. 607/96 |
| 2001/0037104 A1 | 11/2001 | Zhang et al. |
| 2002/0026226 A1 | 2/2002 | Ein |
| 2003/0013998 A1 | 1/2003 | Augustine |
| 2004/0073258 A1 | 4/2004 | Church et al. |
| 2004/0211569 A1 | 10/2004 | Vinegar et al. |
| 2006/0019003 A1 | 1/2006 | Take Xulin Sun et al. |
| 2006/0258962 A1 | 11/2006 | Kopanic et al. |
| 2010/0036445 A1 | 2/2010 | Sakai et al. |

OTHER PUBLICATIONS

International Search Report and Written Opinion issued in PCT/US2012/022252; Applicant: Peter J. Dunbar, mailed Aug. 22, 2012 (15 pages).

* cited by examiner

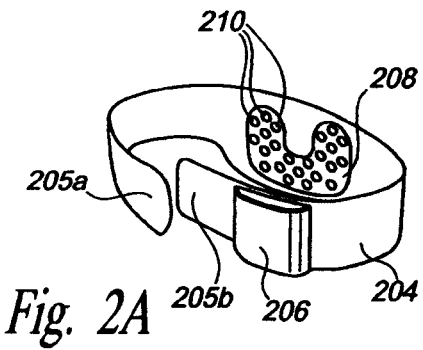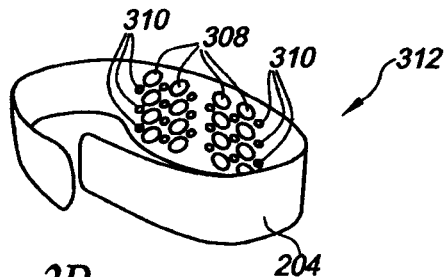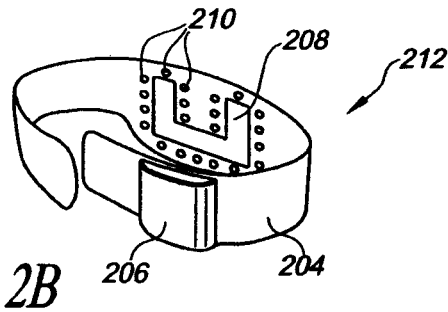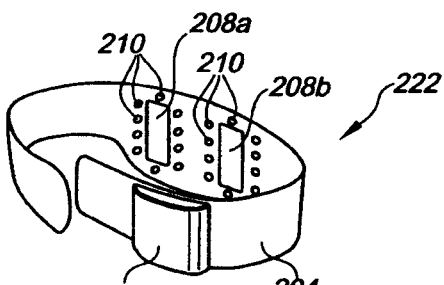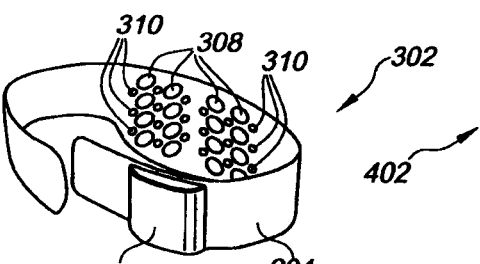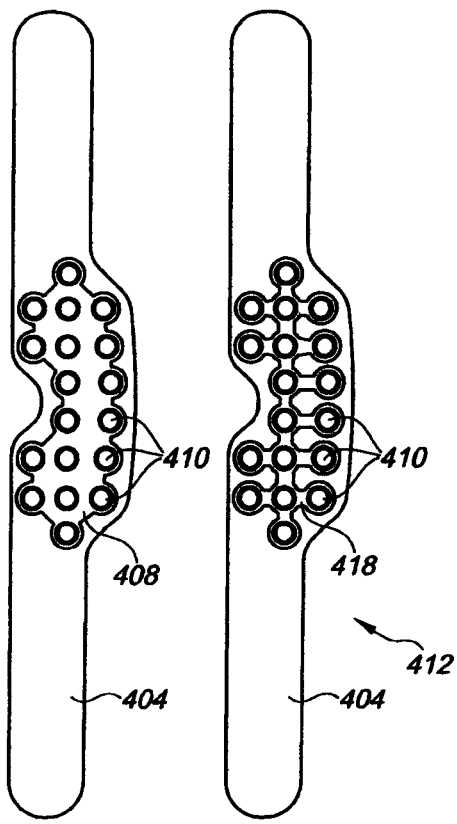

Figure 1: schematic of variables controlled by the laboratory study device.

DEVICES AND METHODS FOR THERAPEUTIC HEAT TREATMENT

CROSS-REFERENCE TO RELATED APPLICATION

The present application claims priority to U.S. Provisional Application 61/012,400, filed on Dec. 7, 2007 and incorporated herein by reference.

TECHNICAL FIELD

The present disclosure is directed generally to therapeutic heat treatment devices and methods combining continuous low temperature heating or cooling with intermittent bursts of high temperature heating, and more specifically, therapeutic heat treatment devices and methods combining continuous low temperature heating or cooling over a selected region with intermittent burst of high temperature heating provided at discrete locations within the low temperature heating region.

BACKGROUND

Heating or cooling devices are commonly used to relieve pain or to treat an injury. Applying a cold pack to an injured ankle, for example, can reduce the swelling in the joint from the injury. Applying heat can also promote the healing and pain relief of different areas of the body. Sore muscles and stiff joints are often treated with a heating pad to increase blood flow and soothe discomfort. For example, many people apply heat to the lower back to relieve back pain. Heat can also be used to provide relief from chronic painful conditions, such as fibromyalgia, rheumatism, arthritis and the like.

There are many existing methods and devices for heating various body parts. For example, electrical heating pads and blankets, disposable pads or patches that generate heat from chemical reactions, microwavable pillows, creams and lotions, water bottles, etc. are all used depending on the body part and user preference. These devices and methods generally provide constant and sustained heat to the affected body part to relax the muscles and associated joints. One drawback of many of these devices, however, is the inability to provide adjustable amounts of heat. Common heat treatment devices, for example, generally provide a single heat level across the device with limited or no adjustability between low, medium and/or high levels of heat.

BRIEF DESCRIPTION OF THE DRAWINGS

In the drawings, the sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIGS. 2A-3B are isometric views,

FIGS. 4A and 4B are top views, and

DETAILED DESCRIPTION

A. Overview

Specific details of several embodiments of the disclosure are set forth in the following description and FIGS. 1A-12 to provide a thorough understanding of these embodiments. A person skilled in the art will understand, however, that the disclosure may be practiced without several of these details or additional details can be added to the disclosure. Moreover, several details describing well-known structures or processes often associated with thermal treatment systems are not shown or described below in detail to avoid unnecessarily obscuring the description of the embodiments of the disclosure. In the Figures, identical reference numbers identify identical, or at least generally similar elements. To facilitate the discussion of any particular element, the most significant digit or digits of any reference number refer to the Figure in which that element is first introduced. For example, element 210 is first introduced and discussed with reference to FIG. 2.

The present disclosure describes several embodiments of heating or cooling pain relief devices and methods and improvements over existing heating and cooling devices. In certain embodiments, for example, a thermal treatment device is configured to apply a continuous amount of low-level heat combined with discrete amounts or intermittent bursts of high-level heat. As described below, the bursts of heat can be at distinct locations within or around the areas producing the low level heat. The low-level heat can be maintained as a constant application of heat while the high-level heat is applied in intermittent bursts (e.g., milliseconds in some embodiments).

Figure 1A:
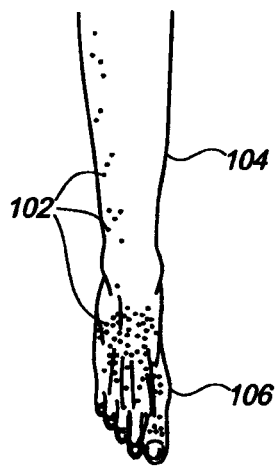
FIG. 1A is an illustration of a mapping of thermal receptors of a human leg and foot.

To better appreciate the benefits of the combination of the continuous low temperature heat and the intermittent high temperature heat, it is helpful to understand the body's reaction to heat. The human body is generally sensitive to heat, with certain body parts having a higher sensitivity than other body parts. The body's sensitivity to heat is recognized by thermal receptors located in the skin and subcutaneous tissue. FIG. 1A illustrates a mapping of the thermal receptors 102 of a human leg 104 and foot 106. As shown in FIG. 1A, the receptors 102 have defined receptive fields with little overlap between the fields. The receptors 102 are excited by heat that is applied to the skin. When the receptors 102 become excited from the applied heat, they send signals to stimulate the brain. The brain can accordingly coordinate other bodily functions in response to the signals sent from the receptors 102. For example, the brain can signal to the body to produce endorphins as an analgesic response to the applied heat.

Figure 1B:
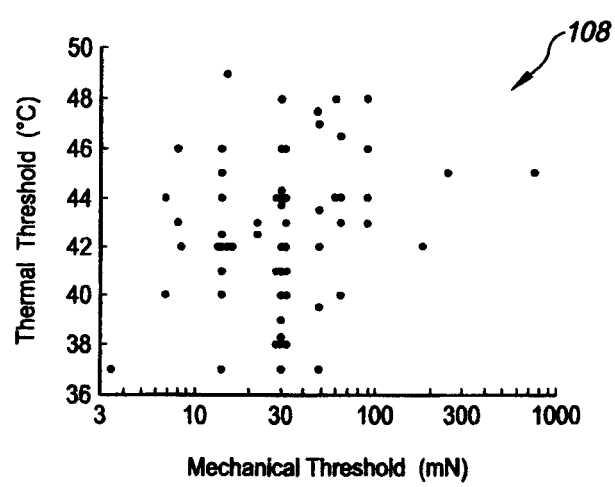
FIG. 1B is a graph of the excitation of thermal receptors versus applied heat.

The thermal receptors located throughout the body can be excited or activated at different temperatures. FIG. 1B, for example, is a graph 108 of the excitation of various receptors versus applied heat. The x-axis of FIG. 1 represents mechanical pressure in mN of excited receptors, and the y-axis represents the temperature in degrees C. of the applied heat. As illustrated by the graph 108, the majority of the excitation of the thermal receptors occurs at temperatures above 42 degrees C., although some excitation does occur at temperatures below 42 degrees C. The excitation also generally peaks below 50 degrees C. Accordingly, in certain embodiments of the present disclosure, bursts of heat in the range of 42-55 degrees C. are applied to discrete areas of skin to excite the receptors. The thermal bursts may be applied in combination with low level heating (i.e., heating below the range of 42-55 degrees C.). In other embodiments, however, the thermal bursts can include temperatures higher or lower than the range of 42-55 degrees C. For the purposes of this disclosure, thermal bursts can be defined as the application of increased heat in discrete areas where the temperature of the burst ranges from 0.1 to 25 degrees C. or more above the baseline temperature of the continuous low-level heat application. The thermal bursts can include a ramp up speed ranging from milliseconds to minutes to reach a maximum temperature. In addition and as described below, the size of the area applying the thermal burst is generally relatively small in comparison to the area applying the low-level heat.

According to one embodiment of the disclosure, a method of applying heat to a living body applying a constant amount of heat to a first defined region of the body at a first temperature. The method also includes applying intermittent amounts of heat to a second defined region of the body. The intermittent amounts of heat may be applied at a second temperature greater than the first temperature. According to further embodiments, the second region overlaps the first region. According to still further embodiments, the intermittent amounts of heat are delivered at pre-selected, focused points wherein the surface area of the second region is smaller than the surface area of the first region.

A method configured in accordance with another embodiment of the disclosure includes a method of exciting thermal receptors in a living organism. The method includes heating a first portion of skin with a generally constant amount of heat at a baseline temperature, and heating a second portion of skin with a burst of heat at a temperature above the baseline temperature while heating the first portion of skin with the generally constant amount of heat.

A device for providing therapeutic heat configured in accordance with still another embodiment of the invention includes a device body configured to provide heat to a portion of skin. The body includes a first low-level heating region for providing a continuous amount of heat at a first temperature. The body also includes a second high-level heating region for providing an intermittent amount of heat (e.g., a thermal burst) at a second temperature greater than the first temperature.

A device for providing therapeutic heat configured in accordance with still another embodiment of the invention includes a device body configured to provide heat to a portion of skin. The body includes a first heat-retaining region for capturing body heat and providing a continuous amount of heat at a first temperature. The body also includes a second high-level heating region for providing an intermittent amount of heat (e.g., a thermal burst) at a second temperature greater than the first temperature. According to still further embodiments, the intermittent amounts of heat are delivered by heating pads less than 2" by 2" is size.

B. Embodiments of Low-Level Heating and Cooling Combined with Intermittent High-Level Heating FIGS. 2A-2C are isometric views of heating wraps or pads 202, 212 and 222, respectively, illustrating various embodiments combining low-level heating with intermittent amounts of high level heating configured in accordance with several embodiments of the disclosure. One skilled in the art will appreciate that devices configured to apply cooling can also be combined with the intermittent high-level heat and be substituted for any of the illustrated heating pads. In FIG. 2A, the heating pad 202 includes a body 204 having opposing end portions 205 (identified individually as a first end portion 205a and a second end portion 205b) to facilitate attachment of the heating pad 202 to a human body. For example, the heating pad 202 can be used on a person's back, arm, leg, etc. The end portions 205 can include various attachment mechanisms, such as hook and loop closures, magnets, buckles, adhesives, etc. One skilled in the art will appreciate that the illustrated heating pad 202 and body 204 are merely representative of one type of heating pad and that the disclosure is not limited to the illustrated shapes and/or configurations in the Figures. For example, heating pads including features disclosed herein can include different shapes or configurations to accommodate different body parts or areas of the body.

The illustrated heating pad 202 also includes a power source 206 operably coupled to a low-level heating region 208 having a generally U-shaped configuration and a plurality of discrete high-level heating areas 210. The power source 206 can include batteries, an electrical connection to line power or any other suitable source of power. In the embodiment illustrated in FIG. 2A, the high-level heating areas 210 are arranged within a footprint of the low-level heating region 208. Alternatively, the high-level heating areas 210 can be arranged on a non-heated heat retaining substrate such that the heat from the human body is retained as the low-level heating regions. In still further embodiments, the high-level heating areas 210 can be individual heating pads arranged independently on a human body. As described below, however, the high-level heating areas 210 can be dispersed in various different patterns and configurations. The low-level heating region 208 is configured to provide a constant and baseline amount of heat to provide pain relief. Each of the high-level heating areas 210 may provide discrete amounts of increased heat for a period of time sufficient to heat the skin or subcutaneous tissue to a desired temperature. For example, the high-level heating areas can apply bursts of heat ranging from 0.1 to 25 degrees C. or more above the baseline low-level heating. In certain embodiments, the high level heating areas 210 provide bursts of heat ranging from 42-55 degrees C.

The size of the individual high-level heating areas 210 is relatively small in comparison to the overall low-level heating region 208 or heat retaining substrate. For example, in certain embodiments, each of the high-level heating areas 210 may cover an area of 3 mm by 3 mm. In other embodiments, these areas may be smaller (e.g., 1 mm by 1 mm) or larger (e.g, 40 mm by 40 mm), however, one skilled in the art will understand that the high-level heating areas 210 may include a variety of configurations and remain within the scope of this disclosure. The relatively small area of the individual high-level heating areas 210 has a low thermal mass that is capable of producing clear and rapid temperature changes. For example, in certain embodiments the high-level heating areas 210 can ramp up to the maximum high temperature in milliseconds. In other embodiments, the ramp up time may be in the range of milliseconds to minutes, and the increased thermal burst can be held for a specified period of time (e.g., milliseconds, seconds, minutes, etc.). The relatively small size of the high-level heating areas 210 also provides several benefits with reference to the power management and conservation. The relatively smaller areas 210, for example, require less power to reach the higher burst temperature.

The combination of the continuous low-level heating and intermittent high-level heating at discrete, focused regions provides several advantages over conventional heating systems. The augmentation of the continuous heating (or cooling), for example, provides enhanced pain relief by promoting blood flow, increasing flexibility and relaxing muscles, ligaments and other tissues. The illustrated configuration achieves enhanced pain relief by providing a strong stimulation of the thermal receptors in the skin and subcutaneous tissues of the body by rapidly changing temperatures. The variations of the temperatures from the thermal bursts reduce or eliminate the accommodation of the receptors to the stimuli. For example, when heat is applied to the body at a constant temperature, the receptors can accommodate the constant heat thus reducing the stimulation. The intermittent bursts of heat, however, can at least partially prevent the receptors from adjusting to the heat by not providing sufficient time for accommodation. This is especially effective when the intermittent bursts of heat are provided by heating pads of a relatively small surface area, for example 2" by 2", or more particularly 1" by 1", or even more particularly, ½" by ½". This is unlike conventional heating systems that do not provide the ability to disrupt the accommodation of the receptors. Accordingly, the intermittent focused bursts of heat, combined with the constant heat, provide for better receptor stimulation resulting in better analgesic results.

The pattern and/or spatial relationship between the low-level heating region 208 and the high-level heating areas 210 can differ in various embodiments according to different body parts and receptor stimulating requirements. In FIG. 2B, for example, the heating pad 212 includes the low-level heating region 208 having a generally rectilinear configuration, and the each of the high-level heating areas 210 is positioned outside of a footprint but proximate to a periphery of the low-level heating region 208. Moreover, in the embodiment illustrated in FIG. 2C, the heating pad 222 includes separate first and second low-level heating regions 208 (identified individually as a first region 208a and a second region 208b) each surrounded by a plurality of high-level heating areas 210.

FIGS. 3A and 3B are isometric views of further embodiments of heating wraps or pads 302 and 312, respectively, including different heating patterns and mechanisms to activate the heating areas. Turning first to FIG. 3A, the heating pad 302 includes the body 204 and the power source 206, similar to the embodiments described above. In this embodiment, however, the high-level heating areas 310 of the heating pad 302 are positioned around and between a plurality of discrete low-level heating regions 308. Although the low-level heating regions 308 do not form a single relatively large area to apply the continuous low-level heat, the total area of the low-level heating regions 308 may still be significantly greater than the high-level heating areas 310. Moreover, in certain embodiments the low-level heating regions 308 can provide heat from a chemical reaction, and the high-level heating areas 310 may be operably coupled to the power source 206 such that only the high-level heating areas 310 are electrically powered. In other embodiments and as illustrated in FIG. 3B, a heating pad 312 may not include an electrical power source such that the heat from the low-level heating regions 308 and the high-level heating areas 310 is created from a chemical source (e.g., a chemical reaction).

FIGS. 4A and 4B are top views of heating wraps or pads 402, 412, respectively, illustrating different configurations of continuous low-level heating regions and high-level heating areas. The heating pad 402 of FIG. 4A, for example, includes a plurality of discrete high-level heating areas 410 that are generally dispersed in a low-level heating region 408 having a shape conforming generally to a body 404 of the wrap 402. The illustrated low-level heating region 408 generally covers the area of the body 404 between the high-level heating areas 410. As such, the total area of the high-level heating areas 410 is significantly less than the total area of the low-level heating region 408. FIG. 4B illustrates a heating pad 412 that is generally similar to the heating pad 402 of FIG. 4A, except that in the illustrated embodiment the heating pad 412 includes a low-level heating region 418 that does not cover all of the area of the body 404 between each of the high-level heating areas 410. Accordingly, the total area of the low-level heating region 418 may not be significantly greater than the total area of the high-level heating areas 410. For example, in certain embodiments the total area of the low-level heating region 418 may be equal to or less than the total area of the high-level heating areas 410. As a result, the illustrated heating pads 402, 412 and others disclosed herein can be configured to provide different relationships between the amounts of heat delivered from the low-level region and the high-level areas.

Figure 5:
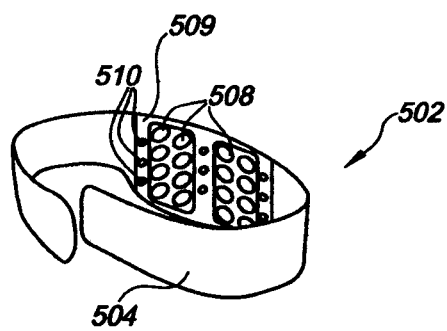
FIG. 5 is an isometric view of heating wraps or pads configured in accordance with embodiments of the disclosure.

In certain embodiments, the high-level heating areas described above can be included as an add-on improvement to existing heating pads, wraps, etc. FIG. 5, for example, is an isometric view of a heating pad 502 including a body 504 having a plurality of continuous low-level heating regions 508. As will be appreciated, the low-level heating regions 508 can be discrete areas or a single larger area as described above. The heating pad 502 can include any commercially available heating wrap, pad, etc. In this embodiment, however, the heating pad 502 includes a plurality of high-level heating areas 510 coupled to the body 504 to provide high temperature thermal bursts to supplement the continuous low-level heating. More specifically, the high-level heating areas 510 can be included in a film 509 that adheres or is otherwise attached to the body 504. Similar to the embodiments described above, the heat from the high-level heating areas 510 can be provided from electrical, chemical or other sources. As such, the high-level heating areas 510 can be added to the heating pad 502 and be positioned on or around the low-level heating regions 508.

Figure 6A:
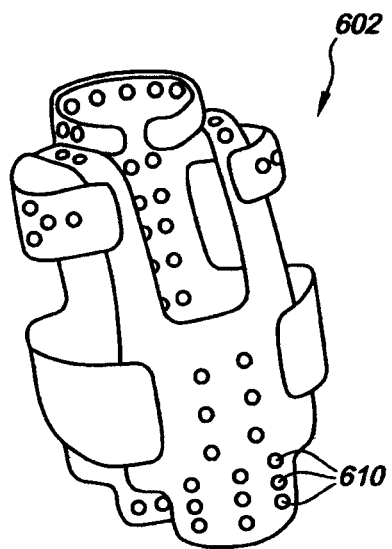
FIG. 6A is an isometric view of a vest.
Figure 6B:
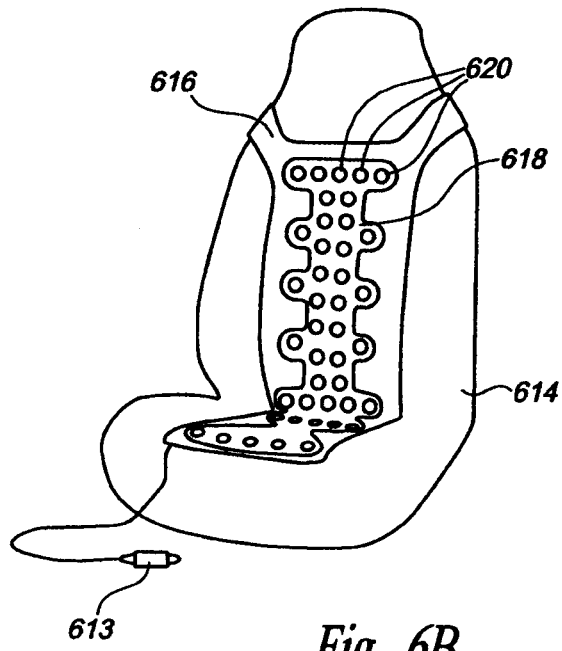
FIG. 6B is an isometric view of a seat cover and FIG. 6C is an isometric view of a brace, each of which is configured in accordance with another embodiment of the disclosure.
Figure 6C:
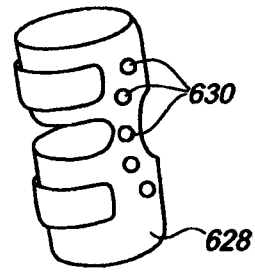

Although several of the embodiments described herein are associated with thermal wraps and pads, the novel intermittent focused thermal bursts combined with continuous low-level heating can be applied to numerous different configurations and applications. FIGS. 6A-6C, for example, illustrate several embodiments of different products incorporating these features. FIG. 6A, more specifically, illustrates an article of clothing, such as a vest 602, having a plurality of discrete high-level heating areas 610. In certain embodiments, the entire vest 602 can be configured to provide continuous low-level heat to a person wearing the vest 602 such that the high-level heating areas 610 can supplement the continuous heat with thermal bursts of higher temperature heat. In other embodiments, discrete portions of the vest 602 can provide the continuous low-level heating. Similar to the embodiments described above, the low and high-levels of heat can be provided from electrical and chemical sources, as well as a combination of these and/or other sources.

FIG. 6B is an isometric view of a chair 614 (e.g., car seat, office chair, etc.) with a seat cover 616 including a continuous low-level heating region 618 combined with a plurality of discrete high-level heating areas 620. The seat cover 616 can include an adapter 613 to draw electrical power from a car or other source for either or both of the low and high-level heating areas 618, 620. FIG. 6C is an isometric view of a brace 628 for a body part (e.g., a knee, ankle, elbow, wrist, etc.) including a plurality of discrete high-level heating areas 630. Accordingly, the brace 628 can be configured to provide the therapeutic low-level heat in combination with bursts of higher temperature heat. More specifically, the brace 628 can be configured to provide the high-level heating areas 630 at focused regions of much smaller surface area than the low level heating areas 618, thus requiring less power and yielding more efficacy in terms of pain relief.

Figure 7A:
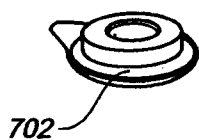
FIG. 7A is an isometric view of a heating patch and FIG. 7B is a back view of a human form with a plurality of attached heating patches configured in accordance with still another embodiment of the disclosure.
Figure 7B:
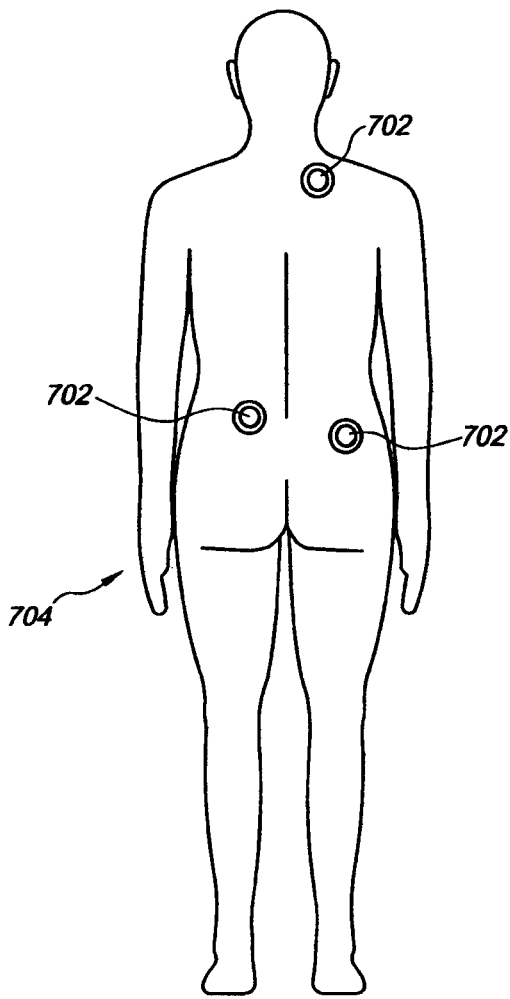
Figure 8:
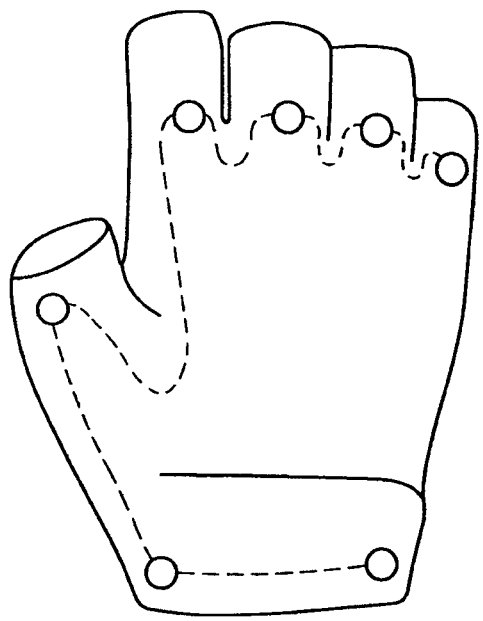
FIG. 8 is an isometric view of a glove including a plurality of heating patches configured in accordance with another embodiment of the disclosure.

FIG. 7A is an isometric view of a single heating patch 702 and FIG. 7B is a back view of a human form 704 wearing a plurality of discrete heating patches 702 (e.g., at the shoulder, lower back, and hip). The heating patches 702 may be configured to provide continuous low-level heating with periodic bursts or impulses of high-level heat, similar to the embodiments described above. In certain embodiments, the heating patches 702 include an adhesive to attach directly to the skin. As a result, the heating patches 702 can be applied simultaneously to various areas of the body and can be used in conjunction with one another or independently to provide pain relief. The illustrated heating patches 702 can accordingly accommodate users who suffer from pain in areas located in more than one region of the body thus requiring simultaneous treatment. For example, the treatment of conditions such as fibromyalgia, dysmenorrhea, PMS, back and neck pain, sports related injuries, etc. may greatly benefit from heating patches 702 located at different positions to simultaneously treat one or more painful areas. FIG. 8 is an isometric view of a glove including a plurality of heating patches configured in accordance with yet another embodiment of the disclosure.

Figure 9:
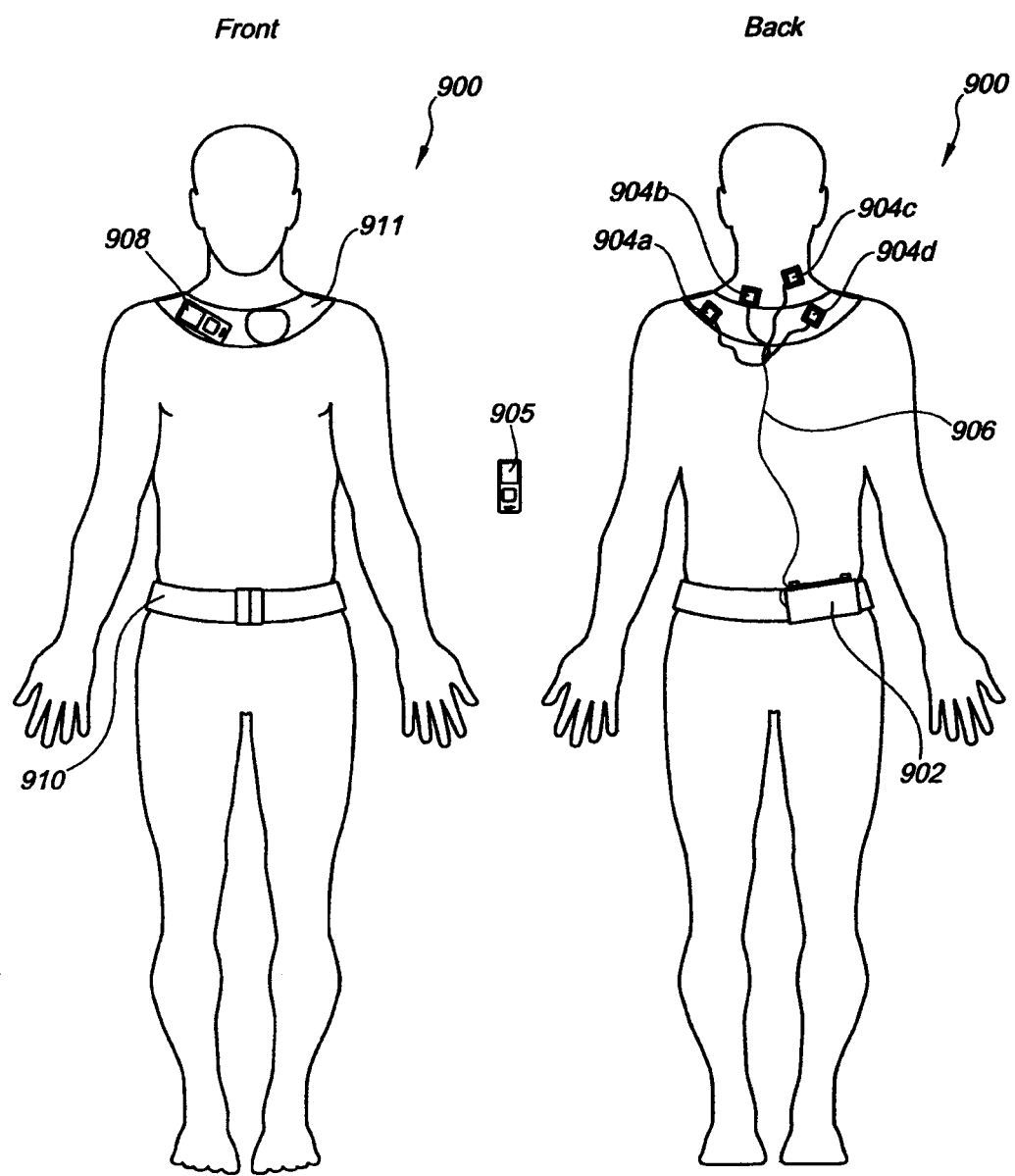
FIG. 9 is a front and a back elevation view of a human wearing a portable system for treating of back pain including a plurality of heating patches configured in accordance with another embodiment of the disclosure.
Figure 10:
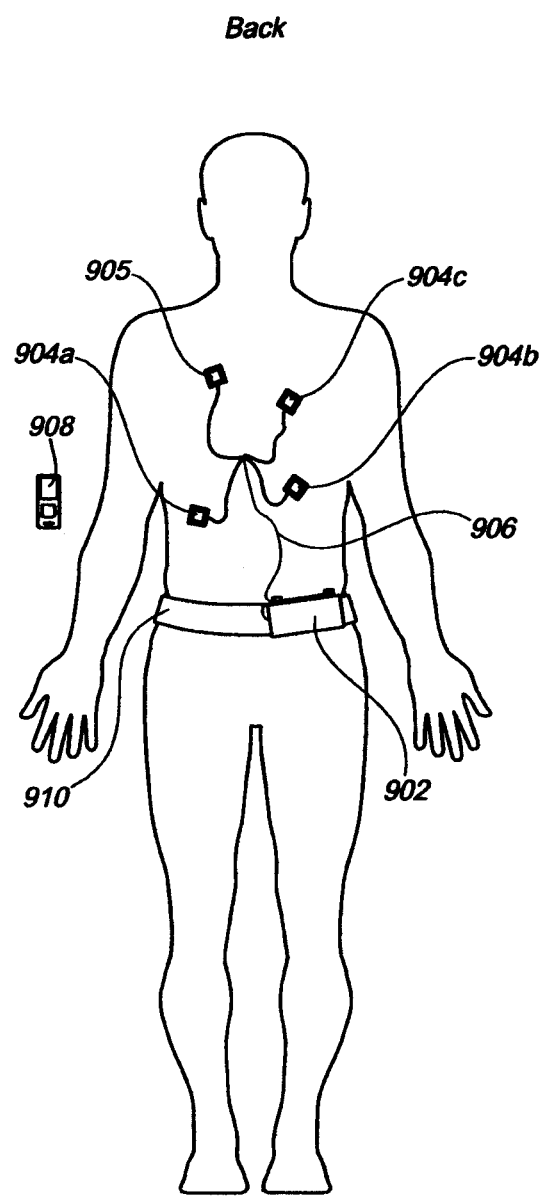
FIG. 10 is a back elevation view of a human wearing a portable system for treating of back pain including a plurality of heating patches configured in accordance with yet another embodiment of the disclosure.
Figure 11:
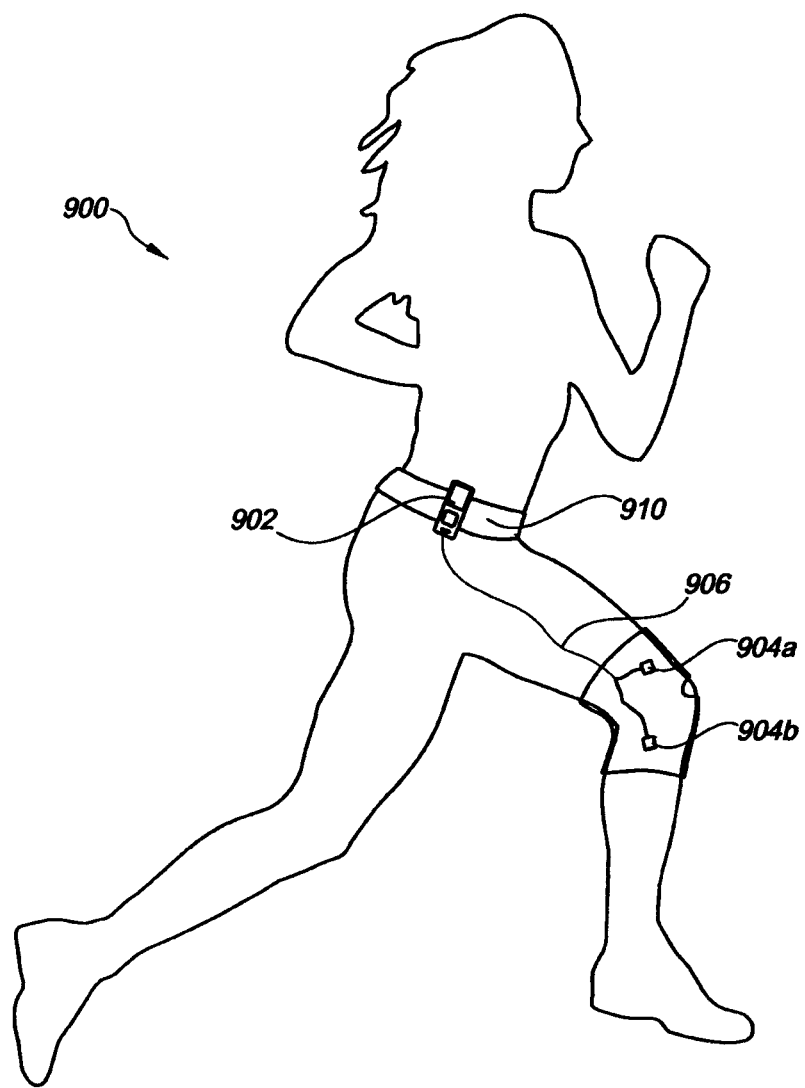
FIG. 11 is a side elevation view of a human wearing a portable system for treating of knee pain including a plurality of heating patches configured in accordance with yet another embodiment of the disclosure.

Further configurations of the device, including those shown in FIGS. 9-11 illustrate the versatility of the system. For example, FIG. 9 includes heating pads 904a-d, electrically connected by wire 906 to a portable power supply 902. The portable power supply 902 and the heating pads 904a-d are each carried by the user by a carrying device 910, 911 such as a belt, pouch, harness or other carrying device. For ease of use, the power supply 902 can be rechargeable. In alternative embodiments, the portable power supply is replaced by a power cord having a plug (not shown for purposes of clarity). In still further embodiments, the system 900 includes a remote control device 908. FIG. 10 illustrates an alternative heating pad 904a-d placement of the system of FIG. 9 and also eliminates the remote control carrying device 911. FIG. 11 illustrates yet another embodiment of the system 900, which is shown for use in relieving knee pain.

The embodiments described herein illustrate the versatility of the various and diverse applications of the high-level thermal bursts delivered through small heating pads combined with low-level continuous heating. Although FIGS. 2A-11 illustrate specific embodiments of products utilizing these heating combinations, the present disclosure is not limited to the illustrated embodiments. Rather, the combined intermittent high-level heating and continuous low-level heating described herein can be used with numerous different types of objects, devices, apparatuses, equipment, assemblies, appliance and the like, including both powered and non powered objects. For example, the intermittent high-level heating and continuous low-level heating can be used with, but are not limited to, pillows, travel pillows, various types of clothing, shoes, ski boots, blankets, beds, mattresses, splints, lotions, ointments, rubs, salves, etc.

According to still further embodiments of the invention, the carrying device for the heating system can include garments or pockets in garments to hold the heating pads. A separate garment can be designed specifically to help treat dysmenorrhea by holding the heating pads to the back and anterior abdomen or pelvis. Some of these garments may for example include:

An elastic-like band to provide support to the underlying tissues while combining the effects of pulsed heat.

Garments that include commercially available chemical or microwavable heat packs. The garments support these products while allowing the addition of the heating elements from the disclosed device.

Garments that have the controller battery unit and healing elements built in. This reduces bulk and the need to external wires.

Heating elements that contain the battery, controller and heating element packaged as one unit. The complete unit may attach directly onto the user or to an element of clothing or garment that supports the heater.

According to still further embodiments, the system can exist in at least various configurations and versions, for example:

Boost. A version designed to improve or enhance the effectiveness of chemical heating packs.

Sport. A version designed to for use with sport induced pain and may include braces or other supportive garments.

Medical. A version designed to simultaneously treat multiple sites on the body.

EXAMPLES

According to aspects disclosed herein, and further in accordance with the Examples provided below, the combination of slow ramp up speeds, short bursts of heat, small pad sizes, and/or long soak periods not only proved effective in reducing pain but significantly reduced power consumption requirements and allowed use of small wires instead of thick cords.

In operation, the addition of as little as one degree centigrade increase via the disclosed system to the steady state Thermacare® pad produced a 50% improvement in effect in pain relief. Without being limited by theory, it is believed that this improvement is due to the phenomena of accommodation of the thermal receptors to low level steady heat. When accommodated, these receptors are balanced at the very edge of stimulation. As further shown in the following examples, small amounts of additional heat stimulate the receptors causing them to fire and thereby producing the very pleasant sensation of thermal comfort and pain relief.

The following Examples are for illustrative purposes only.

Example 1

Clinical Trial

Background

Chronic pain is a public health problem that affects many people in all levels of our society. This study funded by the National Institutes of Health addresses the need for better non-pharmacological pain treatment options. These methods include using pulsed heat alone and adding pulsed heat to improve the effectiveness of currently widely used treatments; FDA approved transcutaneous electrical nerve stimulators (TENS) and commercial chemical heat pack (Thermacare, Proctor and Gamble). Advances in thermal-based pain management technology may provide chronic pain suffers new options apart from drugs or procedures.

Heat produces analgesia through recognized physiologic mechanisms including stimulation of thermal receptors that inhibits nociception via the gate-control theory, by increasing blood flow, and by reducing muscular spasm. Similarly transcutaneous electrical nerve stimulators (TENS) reduce pain by electrically "blocking" pain impulses via gating of nociception. Proof of concept study hypothesized that activation of two separate afferent "gating" pathways, c-fiber dependent thermo-receptor from heat and deep tissue large diameter A-beta primary afferents from TENS would produce more analgesia than either heat or TENS used separately. Further hypothesized that heat alone would be as effective as TENS alone in providing pain relief. Both hypotheses are strongly supported.

Follow-Up Clinical Study:

A follow-up clinical trial was performed based on results of an initial proof of concept study. This clinical study used several laboratory test devices created specifically for the clinical study. The study devices were controlled by a laptop computer connected to a central plug-in that supported a variable number of heating pads. The heating pads were of variable shapes and sizes. These study devices allowed the researcher to precisely control and record a wide number of test variables. These variables include:
  Maximum, minimum, and duration of applied heat;
  Characteristic of heat spike including shape of curve and duration of spike;
  Pattern of heat spikes and time heat is not applied (passive cooling);
  Ramp up and down time, t-soak temperature and t-soak time, T-max time, heat cycle, demand cycle and lockout time (see figure one).

The study was done with full Intuitional Review Board (IRB) approval. 30 subjects were recruited from the community and included both those who suffered from chronic pain and normal controls. All subjects underwent testing over a single 90-120 minute period. The testing methods are described below:

First Treatment Section

This section determined the participant's preference of heating pad size, temperature, and method of application.
  1. Participant is shown three sizes of heating pads (small, medium, large).
  2. Each size pad is placed on subject's back or arm.
  3. Temperature of heating pads is incrementally increased as the participant is asked to rate how the temperature feels using standardized comfort and thermal scales
  4. Participant chooses a preferred temperature.
  5. If participants suffers from chronic pain, he/she is asked to rate their pain on a 0-10 scale.
  6. Heat is applied, in random order, as a steady stimulus and alternatively pulsed between skin temperature and the participant's preferred temperature.
  7. Participant selects a preferred pad size.
  8. Participant selects a preferred heat application.
  9. If participants suffers from chronic pain, he/she is asked to rate their pain on a 0-10 scale.

| Preferred Temperature | Temperature | Time worn comfortably (in seconds) | Comfort Scale Rating | More or Less comfortable compared to previous setting? | Thermal Sensation Scale | Pain Scale if Back Pain Present | Too hot for participant? | 0 (terrible) 10 (wonderful) scale | Maximum Time |
|---|---|---|---|---|---|---|---|---|---|
|  | 41/105.8 | 120 | Very comf |  | warm |  | No | 8 | 2 Min |
|  | 42/107.6 | 120 | Comfortable | same | warm |  | No | 8 | 2 Min |
|  | 43/109.4 | 120 | Comfortable | same | warm |  | No | 8 | 2 Min |
|  | 43.5/110.3 | 120 | Comfortable | same | warm |  | No | 8 | 2 Min |
|  | 44/111.2 | 120 | Comfortable | same | warm |  | No | 8 | 2 Min |
| X | 44.5/112.1 | 120 | Comfortable | more | warm |  | No | 8 | 2 Min |
|  | 45/113 | 120 | Just Comf | less | hot |  | No | 7 | 2 Min |
|  | 45.5/113.9 | 115 | Just Comf | less | hot |  | No | 6 | 2 Min |
|  | 46/114.8 | 90 | Just Uncom | less | hot |  | No | 4 | 2 Min |
|  | 46.5/115.7 | 90 | Just Uncom | less | hot |  | No | 4 | 2 Min |
|  | 47/116.6 | 45 | Just Uncom | less | hot |  | No | 4 | 2 Min |
|  | 47.5/117.5 |  |  |  |  |  |  |  | 2 Min |
|  | 48/118.4 |  |  |  |  |  |  |  | 2 Min |

Second Treatment Section

This section is used to determine the number of heating pads preferred by the participant.
  1. 2 pads of preferred size are placed on participant and heated to preferred temperature.
  2. 4 pads of preferred size are placed on participant and heated to preferred temperature.
  3. 6 pads of preferred size are placed on participant and heated to preferred temperature.
  4. Participant selects preferred number of pads.
  5. If participants suffers from chronic pain, he/she is asked to rate their pain on a 0-10 scale.

| | | Record participant's preference for number of pads. Time Start: Time 11:3 End: 0 | | | |
|---|---|---|---|---|---|
| Preferred Number | Number of Pads | Preferred temp from Obj. #1 | Comfort Scale Rating | 0(terrible) to 10(wonderful) | Maximum Time |
| | 2 | | | | 2 Min |
| | 4 | 44.5 | comf. | 7 | 2 Min |
| X | 6 | 44.5 | Very Comf. | 8 | 2 Min |

Third Treatment Section

This section is used to help determine if significant variability in temperature preference exists between individuals.
1. Participants are reminded that the goal of the study is not to determine who can bear the hottest temperature, but to determine the range of temperature he/she finds comfortable.
2. Preferred pad size and number are placed on participant.
3. Temperature of pads is gradually increased.
4. Participant tells RA to stop when pads become uncomfortable or a maximum of 49 degrees is reached.
5. If participants suffers from chronic pain, he/she is asked to rate their pain on a 0-10 scale.

Fourth Treatment Section

This section is used to determine if subjects prefer steady or pulsed heat and if pulsed heat improves the effectiveness of continuous low level heat.
1. Participants are fitted with a commercial chemical heat pack (e.g., Thermacare®).
2. Measurements are taken in terms of the heat of the chemical pad.
3. Comfort, thermal and pain ratings are taken after which the participant is fitted with the study device using either 2 or fours pads.
4. Temperature of heating pads is incrementally increased as the participant is asked to rate how the temperature feels using standardized comfort and thermal scales
5. Participant chooses a preferred temperature.
6. If participants suffers from chronic pain, he/she is asked to rate their pain on a 0-10 scale.
7. Heat is applied, in random order, as a steady stimulus and alternatively pulsed between skin temperature and the participant's preferred temperature.
8. Participant selects a preferred pad size.
9. Participant selects a preferred heat application.
10. If participants suffers from chronic pain, he/she is asked to rate their pain on a 0-10 scale.

| | | | | | | | | | |
|---|---|---|---|---|---|---|---|---|---|
| | | | | Objective #2: Best t-max and soak temperatures Time Start: Time End: | | | | | |
| Preferred | Peak T-max setting | Low T-max setting | T-max time | Detect Pulse? | Peak T-soak setting | Low T-soak setting | T-soak time | Comfort Scale Ratings | 0(terrible) to 10 (wonderful) |
| | 42 | 41 | 15 seconds | Yes/No | 42 | 40 | 30 sec | Comf | 7 |
| | 43 | 41 | 15 seconds | Yes/No | 42 | 40 | 30 sec | Comf | 7 |
| | 43.5 | 40 | 15 seconds | Yes/No | 42 | 40 | 30 sec | Comf | 7 |
| X | 44 | 40 | 15 seconds | Yes/No | 42 | 40 | 30 sec | Comf | 7 |

Note:
Tmax spike duration 2 seconds and Tsoak spike duration 2 seconds. Run each setting for 90 seconds.
Comments:
setting 1:
setting 2:
setting 3
setting 4:

| | | | | | | | | | |
|---|---|---|---|---|---|---|---|---|---|
| | | | | Heating device used in conjunction with ThermaCare Time Start: Time End: | | | | | |
| Preferred | Peak Tmax setting | Low Tmax setting | Tmax Time | Detect Pulse? | Estimated number of pulses felt | Peak/Low T-soak setting | T-soak time | Comfort Scale Ratings | 0 (terrible) to 10 (wonderful) |
| | 42 | 41 | 15 seconds | Yes/No | | 42/40 | 30 sec | Comf | 8 |
| X | 43 | 41 | 15 seconds | Yes/No | | 42/40 | 30 sec | Comf | 8 |
| | 43.5 | 40 | 15 seconds | Yes/No | | 42/40 | 30 sec | Comf | 7 |
| | 44 | 40 | 15 seconds | Yes/No | | 42/40 | 30 sec | Comf | 7 |

Note:
Tmax spike duration 2 seconds and Tsoak spike duration 2 seconds. Run each setting for 90 seconds.
Comments:

Exit Interviews

After the entire session Exit Interviews were conducted to determine effectiveness of each variation tested.

Results

The following table is a composite result of study subject (N=25 subjects) comfort curves. Most participants found temperatures above 48 degrees too hot. Most subjects preferred temperatures at 46 degrees or below. The median temperature for maximum comfort was 43 degrees above which subjects reported less pleasant sensations. The maximum temperature preferred by any subject (N=1) was 48 degrees. The minimum temperature preferred by any subject was 41.5 degrees. No subject preferred 40 degrees. These findings have important implications for reduced power consumption and the need for individual controllability. The results also support that concept that for maximum effect subjects should be able to "tune" the temperature and thermal characteristics to match their thermodynamic profile. This profile is likely influenced by skin thickness, body fat, local blood flow, underlying pain and the thermal sensitivity of an individual's thermal receptors located in the dermal layers of the skin.

TABLE ONE

Thermal and comfort results for 25 subjects.

| Temperature | Time | Comfort level |
| --- | --- | --- |
| 50 degrees C. | <1 second | Too hot |
| 49.5 degrees C. | <1 second | Too hot |
| 49.0 | <1 second | Too hot |
| 48.5 | <1 second | Too hot |
| 48 | 15 seconds | Then too hot |
| 47.5 | 36 seconds | Then too hot |
| 47 | 52 seconds | Then too hot |
| 46 | 120 seconds | Never too hot |

Results for Pad Size

The study determined that heating pad size less than ½ inch by ½ inch did not result in pain relief. In fact the ½ inch pad size caused thermal burns without provoking the sensation of warmth. This is likely due to the fact that the pad size was smaller than the ability of humans to detect temperature changes due to the corresponding size of the thermal receptive fields.

Pads 1 inch×1 inch produced the best results with the least amount of energy required to power the heating pads. Pads above 1 inch e.g., 1.5 inch×1.5 inch also were effective at reducing pain but were not necessarily more effective than the smaller pads and required more electrical power to function.

Pad Separation was Studied 1 inch×1 inch pads placed less than 6 inches apart were indistinguishable from a single large pad placed across the entire back. At distances greater than 6 inches apart subjects were able to distinguish two separate pads. Without being bound by theory, this lack of discrimination was thought to be due to the size of the human thermal receptive fields on the truncal surfaces. Receptive fields are much smaller on the face and hands. The use of the spatially separated smaller pads (less than 1.5 inches and greater than 0.5 inches) resulted in significant power savings.

Pad Separation Enhances the Effect of Proximal Heating Pads 1 inch×1 inch pads (pads A) placed on a body region (i.e. low back) produced pain relief and the sensation of comfort in the subjects. A second set of 1×1 pads (Pads B) placed on a separate body location greater than 12 inches from the treated body part (Pads A) caused the pain relief and sensation of comfort produced by Pads A to be greatly enhanced. This finding of heating a distant non-painful body part to enhance the thermal analgesia of a separately treated body part has important therapeutic implications. 75% of subjects who had a painful body part treated noted this beneficial effect.

Pulsed Heat Characteristics

The effectiveness and characteristics of heat pulses were studied.

The duration of the heat spike is important. Heat spike duration is defined as the time required to reach t-max plus the duration at T-max in seconds. No subject preferred a shorter heat spike of 0.5 seconds. 10% of subjects preferred a heat spike duration of 1 second. 90% of subjects preferred a heat spike that lasted 2 seconds.

The shorter the duration of the heat spike the hotter maximum temperature is required to produce pain relief. Longer heat spike duration results in lower required maximal temperatures to produce a given state of comfort.

The ratio of peak to trough of the heat spike was important. A separation of 2 degrees from peak to trough was detectable by all subjects. Less than 2 degrees separation was not detectable by subjects.

Subject comfort is determined by the peak of heating not by the temperature of the trough.

100% of subjects preferred the temperature spikes over the steady heat.

Subjects (100%) strongly preferred a pulsed soak cycle over a steady no-pulsed soak cycle.

The addition of the soak cycle reduced power requirements without reducing analgesic effectiveness.

The initial ramp up speed and ramp up time to the first T-max was studied. 100% of subject reported an initial ramp up speed of less than 15 seconds caused a "Burning sensation" that was painful. Initial ramp times greater than 15 seconds did not produce the painful sensation. In all cases the maximum temperatures were the same. Ramp up times greater than 30 seconds also produced painful sensations. Therefore there is an optimal window between 15 and 30 seconds that produces comfort.

Steady Low Level Heat Versus Pulsed Heat

All subjects reported that pulsed heat added to the Thermacare product produced enhanced analgesia. There was a therapeutic window associated with this effect. The Thermacare product produced temperatures in the range around 40 degrees. The addition of as little as 1 degree of temperature rise produced by the study device enhanced the effectiveness of the Thermacare product by 50%. This enhancement occurred over a temperature range of 1-2.5 degrees above which subjects reported no enhancement or even unpleasantness. This therapeutic window is thought to be produced by the thermal energy already added to the body by the Thermacare product. Additional temperature added by the study device efficiently enhances analgesia but can quickly produce pain if the therapeutic window is exceeded. This enhancement of analgesia by as little as one degree was produced only when the additional heat was ramped up over less than a 30 second period. Slower ramp up times produced a lesser effect likely due to the body's ability to accommodate to this additional heat. This finding has important implications for treatment parameters and for energy efficiency.

Heat and Soak Cycle Results

Figure 12:
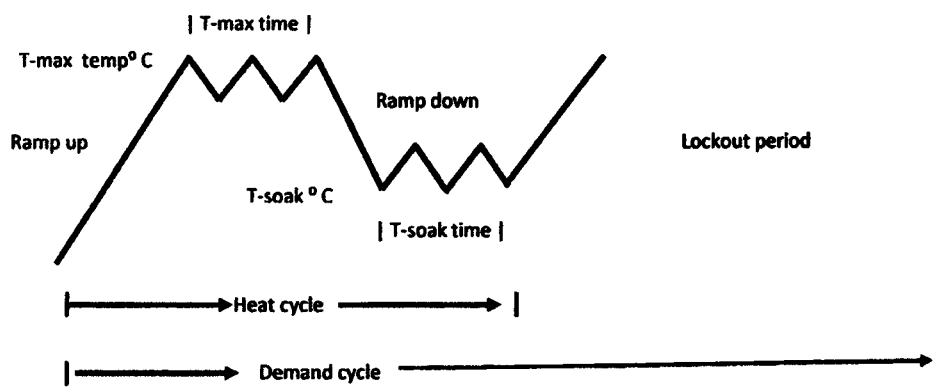
FIG. 12 is a schematic of variables controlled by the laboratory study device in accordance with another embodiment of the disclosure.

As shown further in FIG. 12, once activated, the study device produced a series of heating cycles. The heating cycle is composed of a ramp up time, a t-max time, a ramp down time and a soak time. The ramp up time, a t-max time, and a ramp down time is called the active heat time. The ratio of the active heat time to the soak time was studied. A ratio of 1:2 or even 1:3 was preferred by study subjects. That is a soak time of twice or even three times the duration of the active heat time was preferred and found effective. A typical effective active heating cycle lasted 15 seconds followed by a 30 second soak cycle. Increasing the ratio by increasing the active heat time produced no enhancement of analgesia and was sometimes reported as unpleasant. This ratio has an important effect on power consumption.

A number of heating cycles strung together is called a demand cycle. The duration of the demand cycle was studied. A minimum demand cycle was determined to be 120 seconds. Demand cycles longer than 300 seconds produced incremental additional benefit. Demand cycles longer than 1000 seconds produced little additional benefit.

Each demand cycle is followed by a lockout interval. During this period subjects could not activate a new demand cycle. The lockout interval ranged from 120-300 seconds. This reduced power consumption and increased safety. 90% of subjects offered that the lockout interval produced a feeling of anticipation towards the next demand cycle thereby enhancing the effect of the study device and reducing the body's ability to accommodate to the thermal analgesia.

1. The chemical heating packs delivered heat that was relatively steady and once stable did not vary more than one degree from the mean temperature. Participants clearly preferred heat that was hotter than that provided by the chemical heating pack.
2. Heat added by the study device improved the effectiveness of the heat supplied by the chemical heating pack as measured by pain ratings, and thermal and comfort rating.
3. Pulsed heat as supplied by the heating device was preferred by participants over both steady heat supplied by the chemical pack and the study device.
4. Pulsed heat as supplied by the heating device improved the effectiveness of the chemical heat device.
5. The participant's preferred heating range approximated a bell shaped distribution that ranged from 41.5 degrees centigrade to 48 degrees centigrade.
6. The preferred temperature both t-max and soak temperatures for any given participant was highly individualized and each participant preferred that the heat applied was customized to his or her individual preferences. This clearly increased the effectiveness of the heat as compared to steady heat from the chemical pack.
7 Customizable heat as delivered by the study device was strongly preferred over steady state heat as delivered by the chemical heating pads. This is felt due to the individual characteristics of thermal heat receptors, skin characteristics, and local blood flow.
8. Pulsed heat delivered during the cooling cycle (soak cycle) was preferred to a cooling cycle with no pulsed heat. Participants could easily differentiate pulsed from steady heat both during the heating and soak cycles.
9. The placement of heating pads on a body part distant to the part of the body with pain greatly improved the effectiveness of the study device. For example if a participant had low back pain adding heating pads to the neck or shoulder (non-painful area) increased the effectiveness of the heating pads placed over the painful area (low back).
10. The size of the heating pad was important. If the pad size was too small the participant could not feel the heat. The pad was likely too small to excite the participant's thermal receptive field.

Example 2

Study Objectives
1. How hot (T-max) do the subjects want the heater? Estimated that it will be in the neighborhood of 43-44 degrees. We do this by generating a comfort curve (steady heat) and by testing pulsed heat. Ask is subject has low back pain at present and to rate pain level on a 0-10 scale. If no back pain, no problem, just note that. We would like to determine if the comfort curves vary between subjects with no pain and subjects with pain.

Place two pads on subject's low back. Use following treatment chart:

| Temperature | Duration of heat stop at 2 minutes | Thermal Comfort scale and Thermal sensation scales or stop if it becomes too hot |
| --- | --- | --- |
| 41 degrees | Up to 2 minutes | Comfort scale and tell us if/when it becomes too hot |
| 42 | Up to 2 minutes | Comfort scale and tell us if/when it becomes too hot |
| 43 degrees | Up to 2 minutes | Comfort scale and tell us if/when it becomes too hot. |
| 44 degrees | Up to 2 minutes | Comfort scale and tell us if/when it becomes too hot |
| 45 degrees | Up to 2 minutes | Comfort scale and tell us if/when it becomes too hot |
| 45.5 degrees | Up to 2 minutes | Comfort scale and tell us if/when it becomes too hot. |
| 46 degrees | Up to 2 minutes | |
| 46.5 | Up to 2 minutes | |
| 47 degrees | Up to 2 minutes | |
| 47.5 degrees | Up to 2 minutes | |
| 48 degrees | Up to 2 minutes | |
| 48.5 degrees | Up to 2 minutes | |
| 49 degrees | Up to 2 minutes | |
| 49.5 | Up to 2 minutes | |
| 50 degrees | Up to 2 minutes | |

Note if subject indicates too hot at 45 degrees repeat heat at ½ degree lower

2. What are the best tmax and soak temperatures? This study tries to narrow the optimal temperature range of the heater. If subject doesn't like setting option to go higher.

Tmax spike 2 seconds and T soak spike duration 2 seconds. First ramp time 15 seconds. Run time is 90 seconds per setting.

| T max settings | Tmax time | Can they detect heat pulses? | T soak settings | T soak time | Rating 0 (terrible) to 10 (wonderful) scale and comments |
| --- | --- | --- | --- | --- | --- |
| 42.1 peak 41 low | 15 seconds | Yes/no | 42/40 | 30 seconds | |
| 43 peak 41 low | 15 seconds | Yes/no | 42/40 | 30 seconds | |
| 43.5 peak 40 low | 15 seconds | Yes/no | 42/40 | 30 seconds | |
| 44 peak 40 low | 15 seconds | Yes/no | 42/40 | 30 seconds | |
| 44 peak 40 low | 15 seconds | Yes/no | | | |

3. Test with Thermacare® product. Do they like it? How hot does it need to be? Repeat study but first place Thermacare® wrap on subject. Wrap must be opened at least 20 minutes prior to study.

Tmax spike 2 seconds and T soak spike duration 2 seconds. Run time 60 seconds per test.

| T max settings | Tmax time | Can they detect heat pulses? | T soak settings | T soak time | Rating 0 (terrible) to 10 (wonderful) scale and comments |
|---|---|---|---|---|---|
| 41 peak/ 40 low 42 peak 41 low | 15 seconds | Yes/no | 42/40 | 30 seconds | |
| 43 peak 41 low | 15 seconds | Yes/no | 42/40 | 30 seconds | |
| 43.5 peak 40 low | 15 seconds | Yes/no | 42/40 | 30 seconds | |
| 44 peak 40 low | 15 seconds | Yes/no | 42/40 | 30 seconds | |

4. How many pads do subjects like? Use optimal setting from first trial. First place two pads then 4 pad then 6 pads. Ask subject to rate how many pads they prefer. Measure distances between pads to determine ability to discriminate.

5. If time permits repeat study 2 over a different part of the body and/or neck. Do the comfort curves vary between parts of the body (low back versus neck)? Effect of separating pads?

Conclusion

From the foregoing, it will be appreciated that specific embodiments of the disclosure have been described herein for purposes of illustration, but that various modifications may be made without deviating from the spirit and scope of the disclosure. For example, the high-level heating areas may have other configurations or include more applications than those illustrated in the Figures. Moreover, specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure. Accordingly, embodiments of the disclosure are not limited except as by the appended claims.

Where the context permits, singular or plural terms may also include the plural or singular term, respectively. In addition, unless the word "or" is expressly limited to mean only a single item exclusive from the other items in reference to a list of two or more items, the use of "or" in such a list is to be interpreted as including (a) any single item in the list, (b) all of the items in the list, or (c) any combination of the items in the list. Furthermore, the term "comprising" is used throughout to mean including at least the recited feature(s) such that any greater number of the same feature or additional types of features are not precluded.

We claim:

1. A method of applying heat to a living body, the method comprising:

applying a heat to a first area of the body, wherein the heat is applied by at least one first heating element at a first preset temperature; and applying intermittent amounts of heat to a plurality of second areas of the body by at least one second heating element at a second preset temperature greater than the first preset temperature, wherein the intermittent amounts of heat at the second areas of the body start and end while the heat is applied to the first area of the body, and wherein an individual first heating element is at least approximately twice as large as an individual second heating element.

2. The method of claim 1 wherein the individual second heating elements is generally round and less than approximately two inches in diameter.

3. The method of claim 1 wherein a plurality of second heating elements are distributed over the living body.

4. The method of claim 1 wherein the first area of the body and the second areas of the body are mutually exclusive.

5. The method of claim 1 wherein at least one of the plurality of the second areas at least partially overlaps with a portion of the first area.

6. The method of claim 1 wherein the second heating element is proximate to the first heating element.

7. The method of claim 1 wherein the first area includes two or more discrete areas.

8. The method of claim 1 wherein a total area of the at least one first heating elements in contact with the living body is equal to or less than a sum total area of the at least one second heating elements in contact with the living body.

9. A method of exciting thermal receptors in a living organism, the method comprising:

heating a first portion of skin by at least one first heating element at a first preset temperature; and heating a second portion of skin with a burst of heat by at least one second heating element at a second preset temperature above the first preset temperature, wherein the burst of heat is applied while heating the first portion of skin, wherein the bursts of heat start and end while the heat is applied to the first portion of skin, and wherein an individual first heating element is substantially larger than an individual second heating element.

10. The method of claim 9, wherein the second portion of skin comprises a plurality of discrete individual second portions of skin, and wherein the first portion of skin is substantially larger than individual second portions of skin.

11. The method of claim 10 wherein a sum of the individual second portions of skin is approximately equal in size to the first portion of skin.

12. The method of claim 10 wherein a sum of the individual second portions of skin is larger than the first portion of skin.

13. A device for providing therapeutic heat, the device comprising:

a device body configured to provide heat to a first portion of skin with at least one first heating element and to a second portion of skin with at least one second heating element, wherein the first heating element applied to a low-level heating region of the body is maintained at a first preset temperature, wherein the second heating element applied to a high-level heating area of the body provides an intermittent amount of heat to the second portion of skin at a second preset temperature greater than the first preset temperature while the first heating element is maintained at the first preset temperature, and wherein the first portion of skin is substantially larger than the second portion of skin.

14. The method of claim 13 wherein the second portion of skin comprises a plurality of discrete individual portions of skin.

* * * * *

UNITED STATES PATENT AND TRADEMARK OFFICE
CERTIFICATE OF CORRECTION

PATENT NO.        : 8,579,953 B1
APPLICATION NO.   : 12/330495
DATED             : November 12, 2013
INVENTOR(S)       : Peter J. Dunbar et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 604 days.

Signed and Sealed this
Third Day of March, 2015

Michelle K. Lee
*Deputy Director of the United States Patent and Trademark Office*